United States Patent [19]

Pankavich

[11] B 3,991,204
[45] Nov. 9, 1976

[54] METHOD OF USING BENZOPYRANS AS ANTIPARASITIC AGENTS

[75] Inventor: John Anthony Pankavich, Hamilton Square, N.J.

[73] Assignee: American Cyanamid Company, Stamford, Conn.

[22] Filed: June 17, 1975

[21] Appl. No.: 587,786

[44] Published under the second Trial Voluntary Protest Program on February 17, 1976 as document No. B 587,786.

[52] U.S. Cl. .............................................. 424/281
[51] Int. Cl.² ........................................ A61K 31/37
[58] Field of Search .................................. 424/281

[56] References Cited
UNITED STATES PATENTS

| | | |
|---|---|---|
| 3,511,856 | 5/1970 | McIntyre et al. .................. 424/281 |
| 3,511,896 | 5/1970 | McIntyre et al. .................. 424/281 |

OTHER PUBLICATIONS

Lang et al. Chem. Abst. vol. 80, (1974), p. 133192n.

*Primary Examiner*—Sam Rosen
*Attorney, Agent, or Firm*—Denis A. Polyn

[57] ABSTRACT

This invention relates to a method for the control of helminths in homothermic domestic and farm animals by administering to said animals on anthelmintically effective amount of a benzopyran compound.

8 Claims, No Drawings

METHOD OF USING BENZOPYRANS AS ANTIPARASITIC AGENTS

DESCRIPTION OF THE INVENTION

This invention relates to a method for the control of helminths in homothermic domestic and farm animals by administering to said animals an anthelmintically effective amount of a compound, of the formula (I):

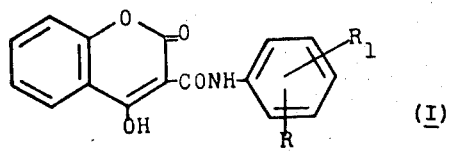

Wherein R and $R_1$ are selected from the group consisting of hydrogen and halogen.

The above-described compounds are highly active when administered orally, intraruminally, intraabomasally intraduodenally or as an implant to homothermic domestic and farm animals such as horses, cattle, sheep, goats, swine, poultry, dogs and cats, and several economically important fur-bearing animals such as mink. They are effective against a variety of helminths, including Haemonchus, Ostertagia, Trichostrongylus, Cooperia, Nematodirus, Oesophagostomum parasitizing the above-said animals.

It has been found that effective helminth control can be achieved in homothermic domestic and farm animals when a compound of formula I is administered as a single dose to said animals at dosage levels of from 1.0 mg/kg to 500 mg/kg of animal body weight and preferably between 10 mg/kg to 150 mg/kg of animal body weight. For single dose administration the active compounds may be formulated as implants, boluses, tablets, pills, injectables and the like, using pharmaceutically acceptable inert diluents and carriers, e.g. dicalcium phosphate, starch, lactose, magnesium stearate, vegetable gums, isotonic saline solution, 0.2 percent agar solution and the like.

Advantageously the active compounds represented by formula (I) can also be administered on a continuing basis, incorporated in the diet of said homothermic animals at anthelmintically effective levels of from 0.005 to 5.0 percent by weight of the feed and preferably between 0.05 to 2.0 percent by weight of the feed. For incorporation in the feed, the active compounds may be formulated as feed premixes or feed supplements containing from about 5 to 25 percent by weight of active compound. The remainder of the feed premix or supplement is usually a mixture of animal nutrients, e.g. soybean meal, ground grain, corn meal, fermentation residues, vegetable oils and the like. The premix or feed supplement is then admixed with the feed of said animals in sufficient amounts to provide the necessary drug concentration in the feed, required to control the helminth infection of said animals.

Formula (I) compounds may be conveniently prepared by reacting 4-hydroxy-2-oxo-2H-1-benzopyran with the appropiately substituted phenylisocyanate in an equimolar ratio, in the presence of a trialkylamine, in a lower alkyl ketone, such as acetone, at reflux till the reaction is essentially complete as determined by the absence of unreacted phenylisocyanate in the reaction mixture. The above reaction sequence may be graphically illustrated as follows:

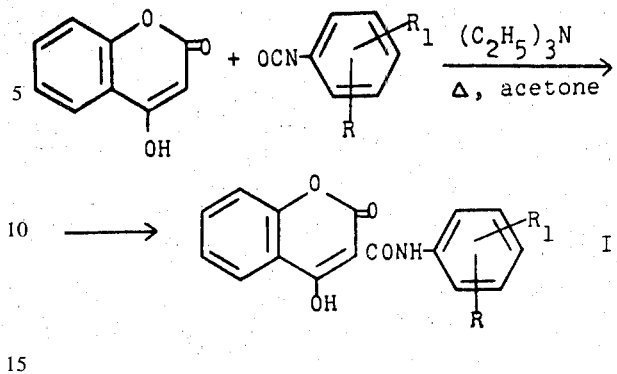

The products thus obtained may be purified by standard laboratory procedures, if necessary, such as recrystallizations, chromatography and the like.

SPECIFIC EXAMPLES

This invention is further illustrated by the following examples which described the preparation of representative compounds and the testing of said compounds.

EXAMPLE 1

Preparation of 3',4'-Dichloro-4-hydroxy-2-oxo-2H-1-benzopyran-3-carboxanilide

To 8.1 g (0.05 mole) of 4-hydroxy-2-oxo-2H-1-benzopyran dissolved in 200 ml acetone is added 5.6 g (0.05 mole) of triethylamine, followed by the addition of 3,4-dichlorophenyl isocyanate. The mixture is heated to reflux, and in ½ hour none of the isocyanate is left as determined by infra-red. The acetone solution is concentrated and the yellow viscous liquid is taken up in chloroform and washed with dilute hydrochloric acid. A white solid precipitates from the chloroform-acid mixture and is collected by filtration. The insoluble white solid is slurried in boiling acetone to yield 11.0 g of pure white powder, the product, m.p. 227°C to 228°C.

EXAMPLES 2 to 8

By the method of Example 1, the following substituted 4-Hydroxy-2-oxo-2H-1-benzopyran-3-carboxanilides are prepared

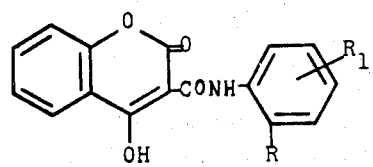

| | R | $R_1$ | m.p. °C. |
|---|---|---|---|
| Example 2. | H | 3-Cl | 183–184 |
| Example 3. | H | 4-F | 187–189 |
| Example 4. | H | 3-F | 184–185 |
| Example 5. | F | H | 195–197 |
| Example 6. | F | 4-F | 200–202 |
| Example 7. | F | 5-F | 192–195 |
| Example 8. | Cl | 4-Cl | 242.5–244 |

EXAMPLE 9

Efficacy of 4-Hydroxy-2-oxo-2H-1-benzopyran-3-carboxanilide derivatives against various helminths in mice Six weeks old Swiss Webster mice are orally inoculated with Nematospiroides dubius, Hymenolepis nana and Aspicularis tetraptera. Eighteen days postinoculation the mice are treated with the appropriate drug diet level for 7 days. For single oral dose administration the compound is thoroughly mixed with 0.1 percent agar and orally intubated at the required dosage 22 days postinfection. 10–15,000 Ascaris suum infective eggs are administered to mice after 1 day on diet medication or 3 days prior to single oral dose administration. Determination of efficacy is done by counting all the N. dubius in treated mice versus the control average. For H. nana and A. tetraptera the absence or presence of these parasites in treated mice is the criterion for determining activity. For A. suum activity the following criterion was used. Reduction or elimination of lung pathology and the total number of lung larvae from treated animals was compared to lung larvae recovered from controls. The data are summarized in Table I below.

age worm burden in the treated group with the average worm burden in the control group.

The data obtained, are summarized in Table II below.

Table II

Anthelmintic Evaluation of 3',4'-Dichloro-4-hydroxy-2-oxo-2H-1-benzopyran-3-carboxanilide in Sheep

| Intraruminal Dose mg/kg | % Efficacy | | | |
|---|---|---|---|---|
| | H.c. | T.a. | O.c. | T.c. |
| 50 | 100 | 0 | 86 | 35 |

H.c. = Haemonchus contortus;
T.a. = Trichostrongylus axei;
O.c. = Ostertagia circumcincta;
T.c. = Trichostrongylus colubriformis.

EXAMPLE 11

Evaluation of 3',4'-Dichloro-4-hydroxy-2-oxo-2H-1-benzopyran-3-carboxanilide against Trichlostrongylus colubriformis in the Mongolian Gerbil Monogolian gerbils are inoculated with 2000 T. colubriformis larvae each. Fourteen to 94 days post inoculation the gerbils are treated with the appropiate drug level diet for 6 days. For single oral dose administration the compound is thoroughly mixed with 0.1 percent agar and orally intubated at the required level. After treatment, 24 hour fecal outputs for 3 days are collected from each animal and examined for passage of parasites. Three days post treatment the gerbils are necropsied and examined for parasites. Percent efficacy is calculated using the formula:

$$\% \text{ Efficacy} = \frac{\text{No. of parasites passed}}{\text{No. passed + No. retained}} \times 100$$

The data obtained are given in Table III below.

Table I

Anthelmintic Activity of 4-Hydroxy-2-oxo-2H-1-benzopyran-3-carboxanilide Derivatives in Mice

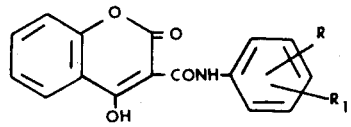

| R | R₁ | % Diet | Drug Diet % Eff. N.d. | No. Mice | mg/kg | Single Oral Dose % Eff. N.d. | No. Mice | A.t. | H.n. | A.s. |
|---|---|---|---|---|---|---|---|---|---|---|
| 3-Cl | 4-Cl | 0.1 | 100 | 8 | | | | A | A | i |
| | | 0.05 | 85 | 20 | | | | i | i | i |
| | | | | | 2000 | 55 | 4 | N.T. | N.T. | A |
| | | | | | 1000 | i | 4 | i | i | A |
| | | | | | 500 | i | 4 | A | i | A |
| | | | | | 100 | i | 4 | A | i | i |
| H | 3-Cl | 0.1 | 65 | 4 | | | | A | A | i |
| | | 0.05 | 46 | 4 | | | | i | i | i |
| H | 4-F | 0.1 | 54 | 8 | | | | i | A | i |
| H | 3-F | 0.1 | 77 | 8 | | | | i | i | i |
| 2-F | H | 0.1 | 66 | 4 | | | | i | i | i |
| 2-F | 4-F | 0.1 | 94 | 4 | | | | A | i | i |
| 2-F | 5-F | 0.1 | 41 | 4 | | | | i | i | i |
| 2-Cl | 4-Cl | 0.1 | 100 | 3 | | | | A | i | i |
| | | 0.05 | 94 | 4 | | | | A | i | i |

% Eff. = Percent Efficacy  A = Active  i = Inactive  NT = Not tested
N.d. = Nematospiroides dubius;
A.t. = Aspicularis tetraptera;
H.n. = Hymenolepis nana;
A.s. = Ascaris suum

EXAMPLE 10

Evaluation (Efficacy) Test in Sheep

Lambs are experimentally inoculated with Haemonchus contortus (H.c.), Trichostrongylus axei (T.a.), Ostertagia circumcincta (O.c) and Trichostrongylus colubriformis (T.c.) species. At patency of the parasites the lambs are treated with 50 mg/kg of body weight with the compound under test administered as an intraruminal injection in 0.2 percent agar. Three days post treatment treated lambs and similary inoculated controls are necropsied and examined for parasites. Percent efficacy is calculated by comparing the aver-

Table III

Efficacy of 3',4'-Dichloro-4-hydroxy-2-oxo-2H-1-benzopyran-3-carboxanilide against *Trichostrongylus colubiformis* in the Mongolian Gerbil

| % Drug in Feed | SOD mg/kg | % Efficacy | Remarks |
| --- | --- | --- | --- |
| 0.05 |  | 82 | × 6 Days |
|  | 100 | 40 |  |
|  | 200 | 100 |  |
|  | 200 | 91 |  |
|  | 500 | 100 |  |

SOD = Single Oral Dose

EXAMPLE 12

Efficacy of 3',4'-Dichloro-4-hydroxy-2-oxo-2H-1-benzopyran-3-carboxanilide against Naturally Occurring Parasitic Infestation in Sheep Lambs naturally infected with a number of parasitic species are treated with 100 mg/kg of body weight with the compound under tested administration as a single oral dose. After treatment, 24 hour fecal outputs for 3 days are collected from each animal and examined for the passage of parasites. Three days post treatment the lambs are necropsied and examined for parasites. Percent efficacy is calculated using the formula:

$$\% \text{ Efficacy} = \frac{\text{No. of parasties passed}}{\text{No. passed} + \text{No. retained}} \times 100$$

The data obtained are summarized in Table IV below.

Table IV

Efficacy of 3',4'-Dichloro-4-hydroxy-2-oxo-2H-1-benzopyran-3-carboxanilide against Naturally Occurring Parasitic Infestation in Sheep

| SOD mg/kg | % Efficacy ||||||
| --- | --- | --- | --- | --- | --- | --- |
|  | T.c. Male | T.v. Male | T. Female | T.a. | C.p. | O.c. | Bun. |
| 100 | 85 | 100 | 80 | 1 | 100 | 0 | 100 |
| 100 | 61 | 79 | 23 | 19.5 | 100 | 100 | 100 |

SOD = Single Oral Dose;
T.c. = *Trichostrongylus colubriformis*;
T.v. = *Trichostrongylus vitrinus*;
T.a. = *Trichostrongylus axei*;
T. = All *Trichostrongylus females*;
C.p. = *Cooperia punctata*;
O.c. = *Oesophagostomum columbianum*;
Bun. = *Bunostomum*

I claim:

1. A method for controlling helminths in a homothermic animal comprising, administering to said animal an anthelmintically effective amount of a compound of the formula:

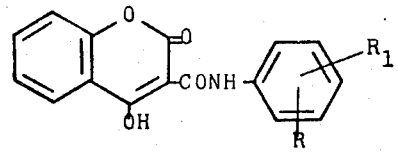

wherein R and $R_1$ are selected from the group consisting of hydrogen and halogen.

2. A method according to claim 1, wherein R is hydrogen, 3-chloro or 2-fluoro and $R_1$ is 3-chloro, 4-chloro, 3-fluoro or 4-fluoro.

3. A method according to claim 1, wherein said compound is 3',4'-dichloro-4-hydroxy-2-oxo-2H-1-benzopyran-3-carboxanilide.

4. A method according to claim 1, wherein said compound is 3'-chloro-4-hydroxy-2-oxo-2H-1-benzopyran-3-carboxanilide.

5. A method according to claim 1, wherein said compound is 3'-fluoro-4-hydroxy-2-oxo-2H-1-benzopyran-3-carboxanilide.

6. A method according to claim 1, wherein said compound is 2',4'-difluoro-4-hydroxy-2-oxo-2H-1-benzopyran-3-carboxanilide.

7. A method according to claim 1, wherein said compound is a component of an animal feed being present in from 0.05 to 2.0 percent by weight.

8. A method according to claim 1, wherein said compound is administered as a single dose of from 1 to 500 mg/kg of body weight of animal.

* * * * *